United States Patent
Matsui (10) Patent No.: US 10,456,037 B2
(45) Date of Patent: Oct. 29, 2019

(54) TERMINAL DEVICE AND INFORMATION PROCESSING SYSTEM

(71) Applicant: OMRON HEALTHCARE CO., LTD., Muko-shi, Kyoto (JP)

(72) Inventor: Toshinori Matsui, Muko (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 0 days.

(21) Appl. No.: 16/144,213

(22) Filed: Sep. 27, 2018

(65) Prior Publication Data

US 2019/0021592 A1 Jan. 24, 2019

Related U.S. Application Data

(63) Continuation of application No. PCT/JP2017/010118, filed on Mar. 14, 2017.

(30) Foreign Application Priority Data

Apr. 8, 2016 (JP) .................................. 2016-077908

(51) Int. Cl.
*A61B 5/00* (2006.01)
*G06Q 50/24* (2012.01)
(Continued)

(52) U.S. Cl.
CPC .............. *A61B 5/0002* (2013.01); *A61B 5/00* (2013.01); *A61B 5/7282* (2013.01); *A61B 5/742* (2013.01);
(Continued)

(58) Field of Classification Search
CPC ....... A61B 5/00; A61B 5/0002; A61B 5/0022; A61B 5/0024; A61B 5/0026;
(Continued)

(56) References Cited

U.S. PATENT DOCUMENTS

2008/0021741 A1* 1/2008 Holla .................... G06F 19/321
  705/3
2009/0058635 A1* 3/2009 LaLonde ............ A61N 1/37282
  340/539.11
(Continued)

FOREIGN PATENT DOCUMENTS

JP H10-155749 A 6/1998
JP 2006-85390 A 3/2006
(Continued)

OTHER PUBLICATIONS

Jun. 6, 2017 Search Report issued in International Patent Application No. PCT/JP2017/010118.

Primary Examiner — Franklin D Balseca
(74) Attorney, Agent, or Firm — Oliff PLC (57) ABSTRACT

A terminal device is provided which is configured to be able to communicate with a server having a database of biological information measured by a biological information measuring device. The database includes measurement data of biological information of a user of another terminal device that is transmitted from the other terminal device to the server. The terminal device includes a reception unit configured to receive measurement data from the server, a condition determination unit configured to determine whether a health condition of the user is normal or abnormal, based on the measurement data received by the reception unit, and an information output unit configured to output information about a health condition of the user, at least based on a determination result of the condition determination unit.

6 Claims, 7 Drawing Sheets

(51) Int. Cl.
- *G08B 25/04* (2006.01)
- *G16H 40/63* (2018.01)
- *H04Q 9/00* (2006.01)

(52) U.S. Cl.
CPC ............ *G06Q 50/24* (2013.01); *G08B 25/04* (2013.01); *G16H 40/63* (2018.01); *H04Q 9/00* (2013.01); *H04Q 2209/00* (2013.01); *H04Q 2209/10* (2013.01)

(58) Field of Classification Search
CPC ...... A61B 5/7282; A61B 5/742; G16H 40/63; G06Q 50/24; G08B 25/04; H04Q 9/00; H04Q 2209/00; H04Q 2209/10; H04Q 2209/40; H04Q 2209/50; H04Q 2209/70
See application file for complete search history.

(56) References Cited

U.S. PATENT DOCUMENTS

2014/0184422 A1* 7/2014 Mensinger ............ A61B 5/0004
340/870.02
2015/0245189 A1 8/2015 Nalluri et al.

FOREIGN PATENT DOCUMENTS

| | | |
|---|---|---|
| JP | 2014-120173 A | 6/2014 |
| JP | 2015-535411 A | 12/2015 |
| JP | 2016-42630 A | 3/2016 |
| WO | 2014/098415 A1 | 6/2014 |

\* cited by examiner

| DEVICE | TYPE | MEASUREMENT TIMING | NORMAL RANGE | IMPORTANCE |
|---|---|---|---|---|
| SPHYGMOMANOMETER | BLOOD PRESSURE | ALWAYS | 140/90mmHg OR LESS | HIGH |
| THERMOMETER | BODY TEMPERATURE | ALWAYS | 35.5°C~36.5°C | HIGH |
| SLEEP MONITOR | SLEEP DURATION | MORNING | 7 HOURS OR LONGER | INTERMEDIATE |
| PEDOMETER | STEP COUNT | MORNING, NIGHT | 3000 STEPS OR MORE | INTERMEDIATE |
| WEIGHT SCALE | WEIGHT | NIGHT | LESS THAN ±2 KG COMPARED WITH PREVIOUS MEASUREMENT | LOW |

FIG.7

TERMINAL DEVICE AND INFORMATION PROCESSING SYSTEM

The present application is a continuation of International application No. PCT/JP2017/010118, filed Mar. 14, 2017, which claims priority to Japanese Patent Application No. 2016-077908, filed Apr. 8, 2016, the entire contents of each of which are incorporated herein by reference.

BACKGROUND OF THE INVENTION

Field of the Invention

The present disclosure relates to a terminal device and an information processing system.

Description of the Background Art

A variety of measuring devices have been developed for measuring various biological information indicating the current states of human bodies, such as body temperature, blood pressure, pulse, and blood sugar level. Biological information measured by such a measuring device is captured into a terminal device such as a smartphone to check the health condition of the user of the terminal device. In a server for managing the measuring device, biological information obtained by the measuring device is analyzed, and the analysis result is provided to the terminal device.

For example, Japanese Patent Laying-Open No. 2014-120173 discloses a method for managing at least one external device connected to a host terminal through a management server. The method includes a step of acquiring measurement information measured by an external device, a step of requesting authentication from a management server, a step of, if authentication is successful, transmitting the acquired measurement information to the management server, a step of receiving management information for managing at least one external device that is generated based on the measurement information, in the management server, and a step of managing at least one external device based on the received management information. With the recent progress in aging, there have been growing demands for reliably checking not only the user's own health condition but also the other's (in particular, elderlies) health condition. For example, with the widespread use of mobile terminals, a family member can grasp the health condition of a cared person with a terminal by allowing the cared person such as an elderly person to carry another terminal capable of acquiring measurement data of a measuring device.

The technique in Japanese Patent Laying-Open No. 2014-120173 discloses that the management server acquires measurement information measured by an external device (for example, information about the health of the user of the host terminal) through the authenticated host terminal and uses the measurement information to determine the health condition of the user of the host terminal. However, techniques related to the demands described above are never taught.

SUMMARY OF THE INVENTION

The present disclosure is made in view of the foregoing and an object in an aspect is to provide a terminal device and an information processing system capable of improving the convenience in checking the health condition of the user of another terminal device.

According to an embodiment, a terminal device configured to be able to communicate with a server having a database of biological information measured by a biological information measuring device is provided. The database includes measurement data of biological information of a user of another terminal that is transmitted from the other terminal device to the server. The terminal device includes a reception unit configured to receive the measurement data from the server, a condition determination unit configured to determine whether a health condition of the user is normal or abnormal, based on the measurement data received by the reception unit, and an information output unit configured to output information about a health condition of the user, at least based on a determination result of the condition determination unit.

An information processing system according to another embodiment includes a server having a database of biological information measured by a biological information measuring device, and a first terminal device and a second terminal device each configured to communicate with the server. The second terminal device includes a data acquisition unit configured to acquire measurement data of biological information of a user of the second terminal device that is measured by the biological information measuring device, from the biological information measuring device, and an information transmission unit configured to transmit the measurement data acquired by the data acquisition unit to the server. The first terminal device includes a reception unit configured to receive the measurement data from the server, a condition determination unit configured to determine whether a health condition of the user is normal, based on the measurement data received by the reception unit, and an information output unit configured to output information about a health condition of the user, at least based on a determination result of the condition determination unit.

The present disclosure can improve the convenience in checking the health condition of the user of another terminal device.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Embodiments of the present invention will be described below with reference to the figures. In the following description, the same components are denoted by the same reference signs. Their names and functions are also the same. A detailed description thereof therefore will not be repeated.

<System Configuration>

Figure 1:
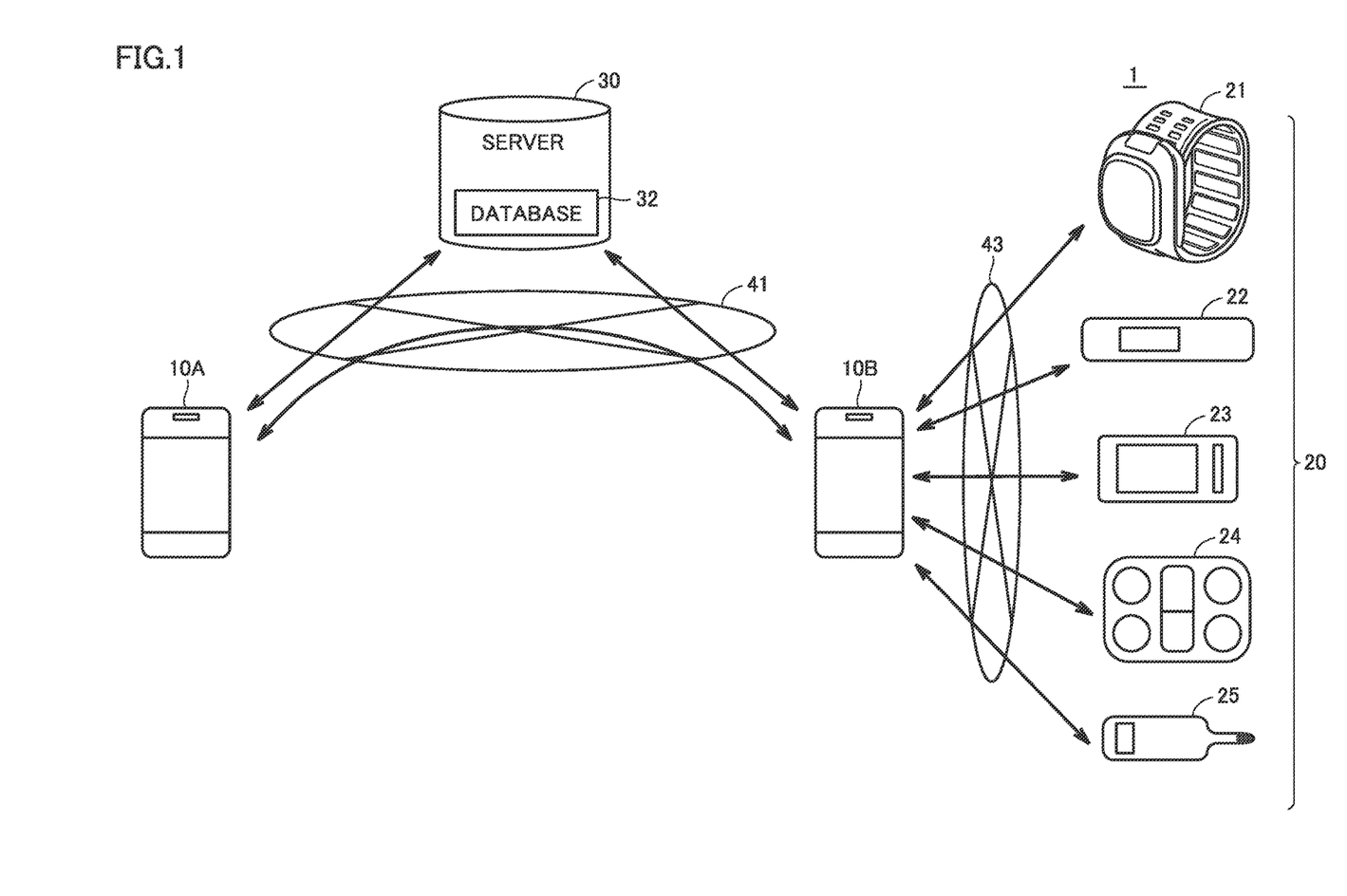
FIG. 1 is a diagram showing an overall configuration of an information processing system according to the present embodiment.

FIG. 1 is a diagram showing an overall configuration of an information processing system 1 according to the present embodiment.

Referring to FIG. 1, information processing system 1 includes terminal devices 10A, 10B serving as user terminals, a sphygmomanometer 21, a sleep monitor 22, a pedometer 23, a weight scale and body composition monitor 24, and a thermometer 25, which are examples of the biological information measuring device for measuring biological information of users, a server 30, and networks 41, 43. In the following description, terminal device 10A is a terminal of a user A (the terminal of a caregiver), and terminal device 10B is a terminal of a user B (the terminal of a care receiver). In the following, for convenience of explanation, terminal devices 10A, 10B may be collectively referred to as "terminal device 10".

The biological information measuring device is not limited to sphygmomanometer 21, sleep monitor 22, pedometer 23, weight scale and body composition monitor 24, and thermometer 25 and may be any device for measuring user's biological information. For example, the biological information measuring device may be an activity tracker. For convenience of explanation, sphygmomanometer 21, sleep monitor 22, pedometer 23, weight scale and body composition monitor 24, and thermometer 25 hereinafter may be collectively referred to as "measuring device 20". Here, sphygmomanometer 21 according to the present embodiment is a wristwatch-type sphygmomanometer in which a main unit and a cuff are integrated. Sphygmomanometer 21 may be worn for a long time like a wristwatch to measure pulsation every pulse for consecutive 24 hours and/or may be always worn to allow the user to push a measurement start button for measurement. Sphygmomanometer 21 thus can always measure the user's blood pressure.

Terminal device 10 is, for example, a smartphone having a touch panel. In the description below, a smartphone is taken as a typical example of "terminal device". However, the terminal device may be any other terminal device such as a foldable mobile phone, a tablet terminal device, a PC (personal computer), or a PDA (Personal Data Assistance).

Network 41 for connecting terminal device 10A, terminal device 10B, and server 30 with each other includes a variety of networks such as the Internet and mobile terminal communication networks. Network 43 for connecting terminal device 10B with measuring device 20 employs a near-field wireless communication scheme, typically BLE (Bluetooth (registered trademark) low energy). However, network 43 is not limited thereto. A wired communication scheme may be employed, or a wireless LAN (local area network) or any other wireless communication schemes may be employed.

Server 30 stores a variety of data transmitted from each terminal device 10. Specifically, server 30 stores a group ID allocated to each group that terminal device 10 belongs to and identification information (terminal ID) of terminal device 10 associated with each other in a database 32. Server 30 also manages a variety of data transmitted from terminal devices 10 for each group ID, using database 32.

Here, in the present embodiment, it is assumed that terminal device 10A and terminal device 10B belong to the same group X. Group ID x of group X is thus associated with terminal ID a of terminal device 10A and terminal ID b of terminal device 10B. Terminal device 10A and terminal device 10B can access server 30 (database 32) using the same group ID x to share a variety of data stored in association with group ID x. For example, measurement data of biological information of user B transmitted from terminal device 10B to server 30 is stored in database 32.

<System Operation Overview>

Figure 2:
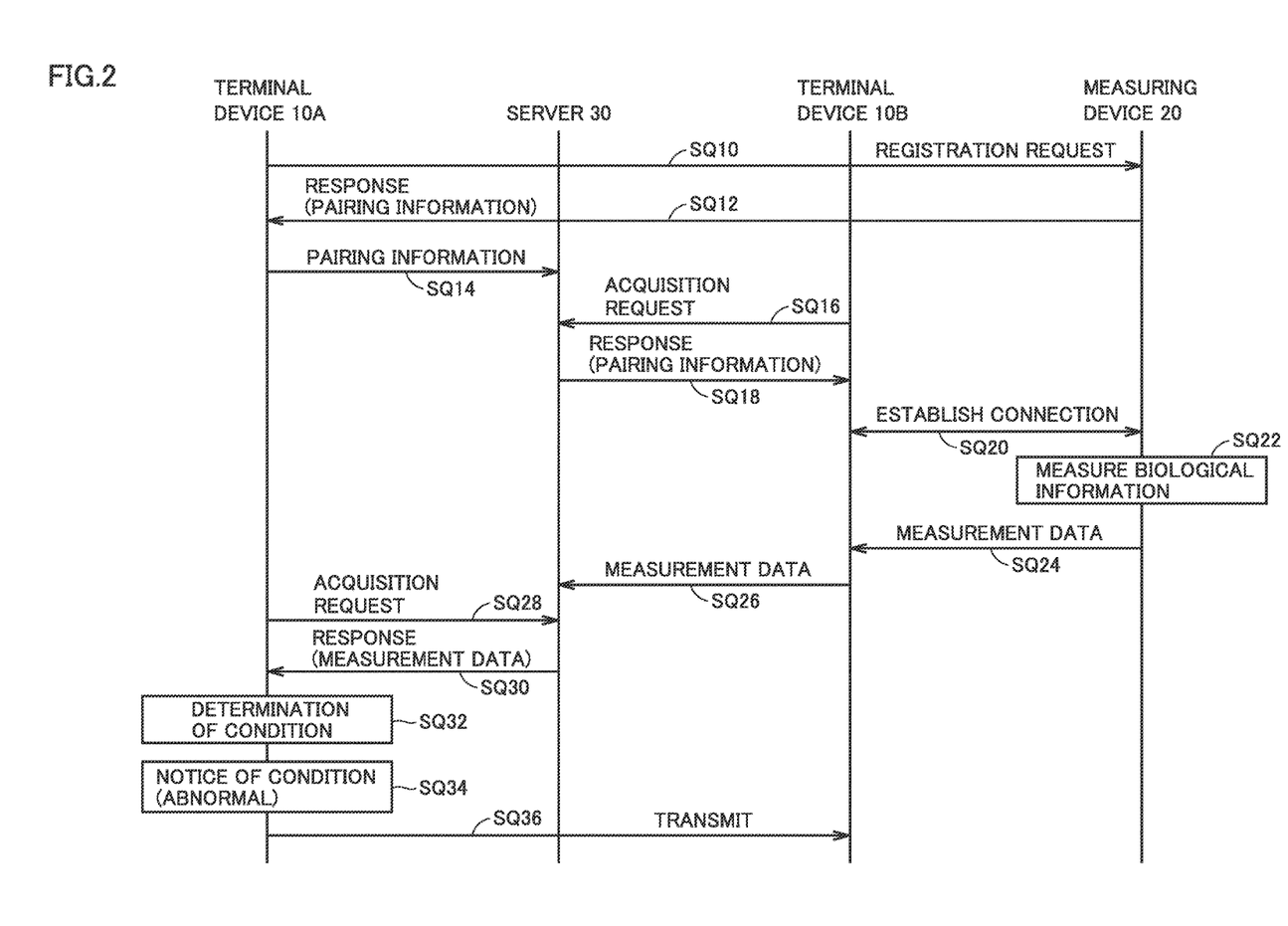
FIG. 2 is a diagram showing an operation overview of the information processing system according to the present embodiment.

FIG. 2 is a diagram showing an operation overview of information processing system 1 according to the present embodiment. Referring to FIG. 2, terminal device 10A makes a registration (paring) request to measuring device 20 (sequence SQ10). The registration request includes terminal ID a of terminal device 10A. In response to the registration request from terminal device 10A, measuring device 20 transmits pairing information to terminal device 10A (sequence SQ12). The pairing information is information necessary for terminal device 10 to establish wireless communication connection with measuring device 20 and includes, for example, the device name, MAC address, and service information of measuring device 20. Terminal device 10 accepts input of a PIN code necessary for pairing from the user and stores the PIN code. For example, the PIN code is printed on the housing of measuring device 20 or displayed on the screen.

Terminal device 10A registers the acquired pairing information in terminal device 10A and transmits the pairing information and terminal ID a to server 30 (sequence SQ14). Server 30 stores the pairing information transmitted from terminal device 10A into database 32 in association with group ID x.

Terminal device 10B makes an acquisition request for data associated with group ID x (sequence SQ16). The acquisition request includes terminal ID b of terminal device 10B. In response to the acquisition request, server 30 transmits pairing information to terminal device 10B (sequence SQ18). Terminal device 10B establishes wireless communication connection with measuring device 20, using the received pairing information (sequence SQ20).

As described above, in the present embodiment, user A acquires pairing information of measuring device 20 for user B (care receiver), using his/her own terminal device 10A, and stores the acquired pairing information into server 30. User B can access server 30 using terminal device 10B and registers the pairing information into terminal device 10B to establish connection with measuring device 20. This eliminates the time and effort of the pairing operation for user B to establish wireless communication connection with measuring device 20.

Measuring device 20 measures biological information of user B (sequence SQ22). Measuring device 20 transmits measurement data of biological information of user B to terminal device 10B (sequence SQ24). Typically, measuring device 20 transmits the measurement data to terminal device 10B when a data transfer request from terminal device 10B is accepted within a predetermined time after the measurement. User B may operate measuring device 20 to transfer the measurement data to terminal device 10B.

Terminal device 10B stores the measurement data received from measuring device 20 into an internal memory and transmits the measurement data to server 30 (sequence SQ26). Terminal device 10A requests acquisition of data associated with group ID x (sequence SQ28). Typically, terminal device 10A executes a data acquisition request to server 30 periodically (for example, every few hours) or at a preset timing (for example, at 7:00 a.m. or 8:00 p.m.). Terminal device 10A may make the acquisition request based on reception of an update notice of data associated with group ID x from server 30.

In response to the acquisition request, server 30 transmits measurement data of biological information of user B received from terminal device 10B to terminal device 10A (sequence SQ30). Terminal device 10A determines whether the health condition of user B is normal, based on the received measurement data (sequence SQ32). When it is determined that the health condition of user B is abnormal, terminal device 10A notifies user A of the abnormal state (sequence SQ34). For example, terminal device 10A displays a warning screen as shown in FIG. 3 on the display.

Figure 3:
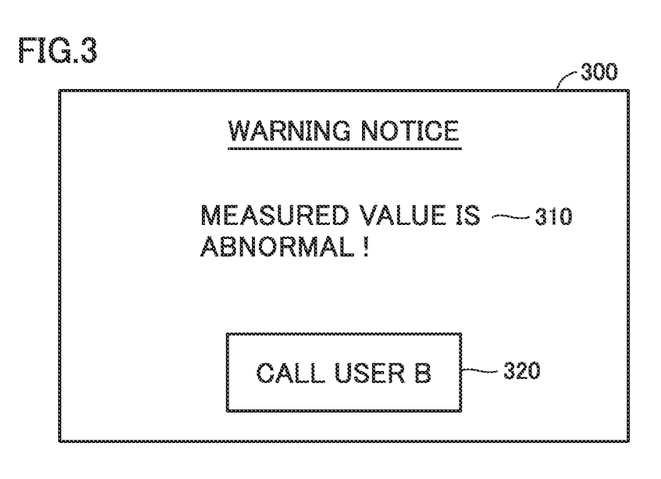
FIG. 3 is a diagram showing an exemplary warning screen according to the present embodiment.

FIG. 3 is a diagram showing an exemplary warning screen according to the present embodiment. Referring to FIG. 3, a warning screen 300 includes information 310 indicating that the measured value of biological information is abnormal and a call button 320 to user B (terminal device 10B).

Referring to FIG. 2 again, when accepting an operation to select call button 320 from user A, terminal device 10A executes a call to terminal device 10B (sequence SQ36).

<Hardware Configuration>
(Terminal Device)

Figure 4:
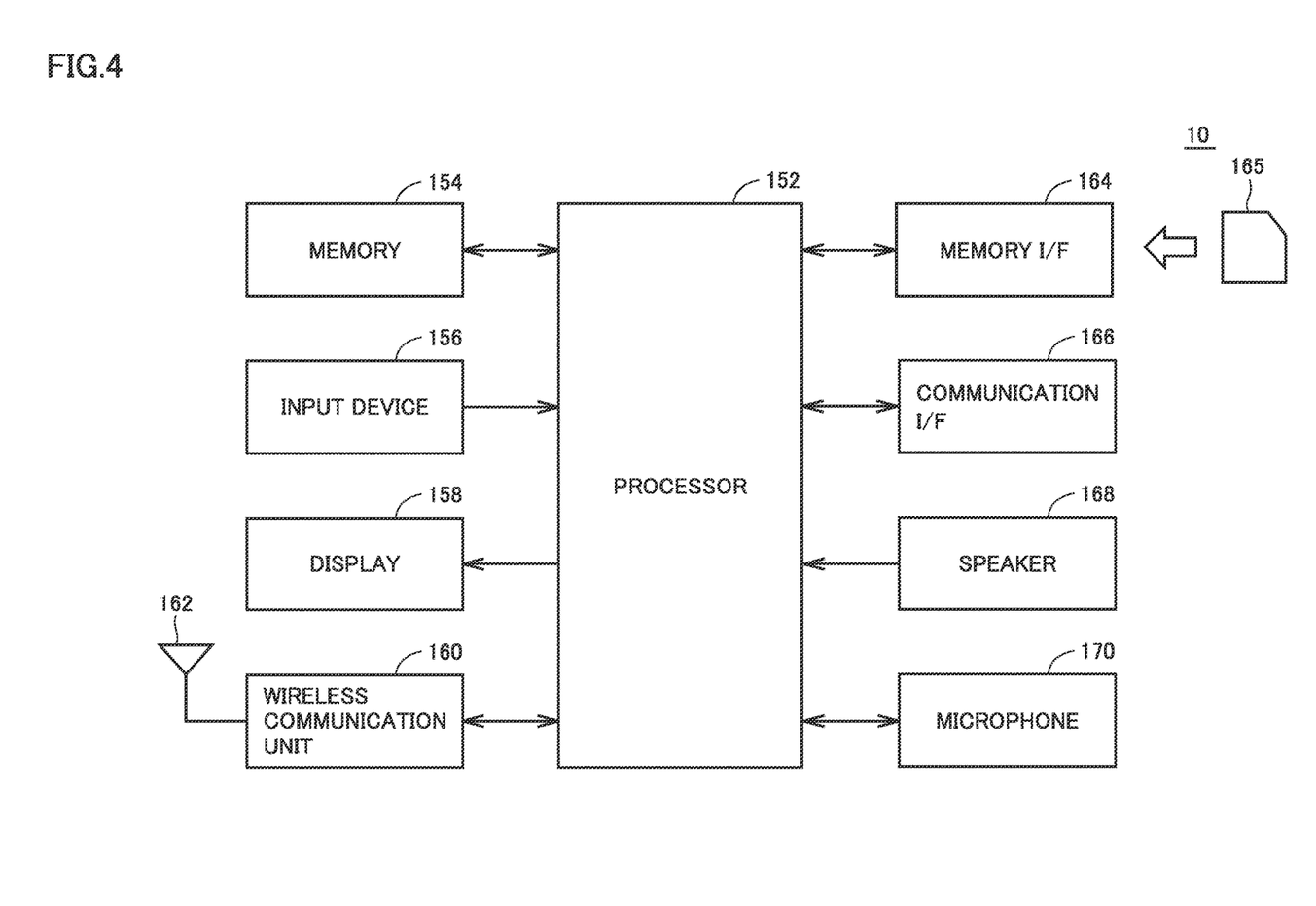
FIG. 4 is a block diagram showing an exemplary hardware configuration of a terminal device according to the present embodiment.

FIG. 4 is a block diagram showing an exemplary hardware configuration of terminal device 10 according to the present embodiment. Referring to FIG. 4, terminal device 10 includes, as main components, a processor 152, a memory 154, an input device 156, a display 158, a wireless communication unit 160, a memory interface (I/F) 164, a communication interface (I/F) 166, a speaker 168, and a microphone 170.

Processor 152 is a typically an arithmetic operation unit such as a CPU (Central Processing Unit) and an MPU (Multi Processing Unit). Processor 152 reads out and executes a program stored in memory 154 to function as a control unit that controls the operation of each unit in terminal device 10. Processor 152 implements each process (step) of terminal device 10 described later by executing the program.

Memory 154 is implemented by a RAM (Random Access Memory), a ROM (Read-Only Memory), or a flash memory. Memory 154 stores a program executed by processor 152 or data used by processor 152.

Input device 156 accepts an operation input to terminal device 10. Typically, input device 156 is implemented by a touch panel. The touch panel is provided on display 158 having the function as a display unit and is, for example, a capacitive touch panel. The touch panel detects a touch operation on the touch panel by an external object at predetermined time intervals and inputs the touch coordinates to processor 152. Input device 156 may include buttons.

Wireless communication unit 160 connects to a mobile communication network through communication antenna 162 and transmits/receives a signal for wireless communication. This enables terminal device 10 to communicate with another communication device (for example, server device 30, another terminal device 10), for example, through a mobile communication network such as LTE (Long Term Evolution).

Memory interface 164 reads out data from an external storage medium 165. Processor 152 reads out data stored in storage medium 165 through memory interface 164 and stores the data into memory 154. Processor 152 reads out data from memory 154 and stores the data into external storage medium 165 through memory interface 164.

Storage medium 165 includes a medium for storing a program in a nonvolatile manner, such as a CD (Compact Disc), a DVD (Digital Versatile Disk), a BD (Blu-ray (registered trademark) Disc), a USB (Universal Serial Bus) memory, and an SD (Secure Digital) memory card.

Communication interface (I/F) 166 is a communication interface for exchanging a variety of data between terminal device 10 and measuring device 20 and is implemented by an adaptor or a connector. In the present embodiment, BLE (Bluetooth (registered trademark) low energy) is employed as a communication scheme. However, the communication scheme may be, for example, a wireless communication scheme via a wireless LAN or may be a wired communication scheme using a USB (Universal Serial Bus).

Speaker 168 converts an audio signal applied from processor 152 into sound for output to the outside of terminal device 10. Microphone 170 accepts an audio input to terminal device 10 and applies an audio signal corresponding to the audio input to processor 152.

(Server)

Server device 30 provides information processing as a whole as described above and as will be described later and may have a known hardware configuration. For example, server device 30 includes a processor for executing a variety of processing, a memory for storing a program and data, a communication interface for transmitting/receiving a variety of data to/from terminal device 10, and an input interface for accepting an instruction from a manager.

(Measuring Device)

Measuring device 20 provides information processing as a whole as described above and as will be described later and may have a known hardware configuration. For example, measuring device 20 includes a processor for executing a variety of processing, a memory for storing a program and data, a communication interface for transmitting/receiving a variety of data to/from terminal device 10, an input interface for accepting an instruction from the user, and a variety of hardware for measuring biological information.

<Functional Configuration>

Figure 5:
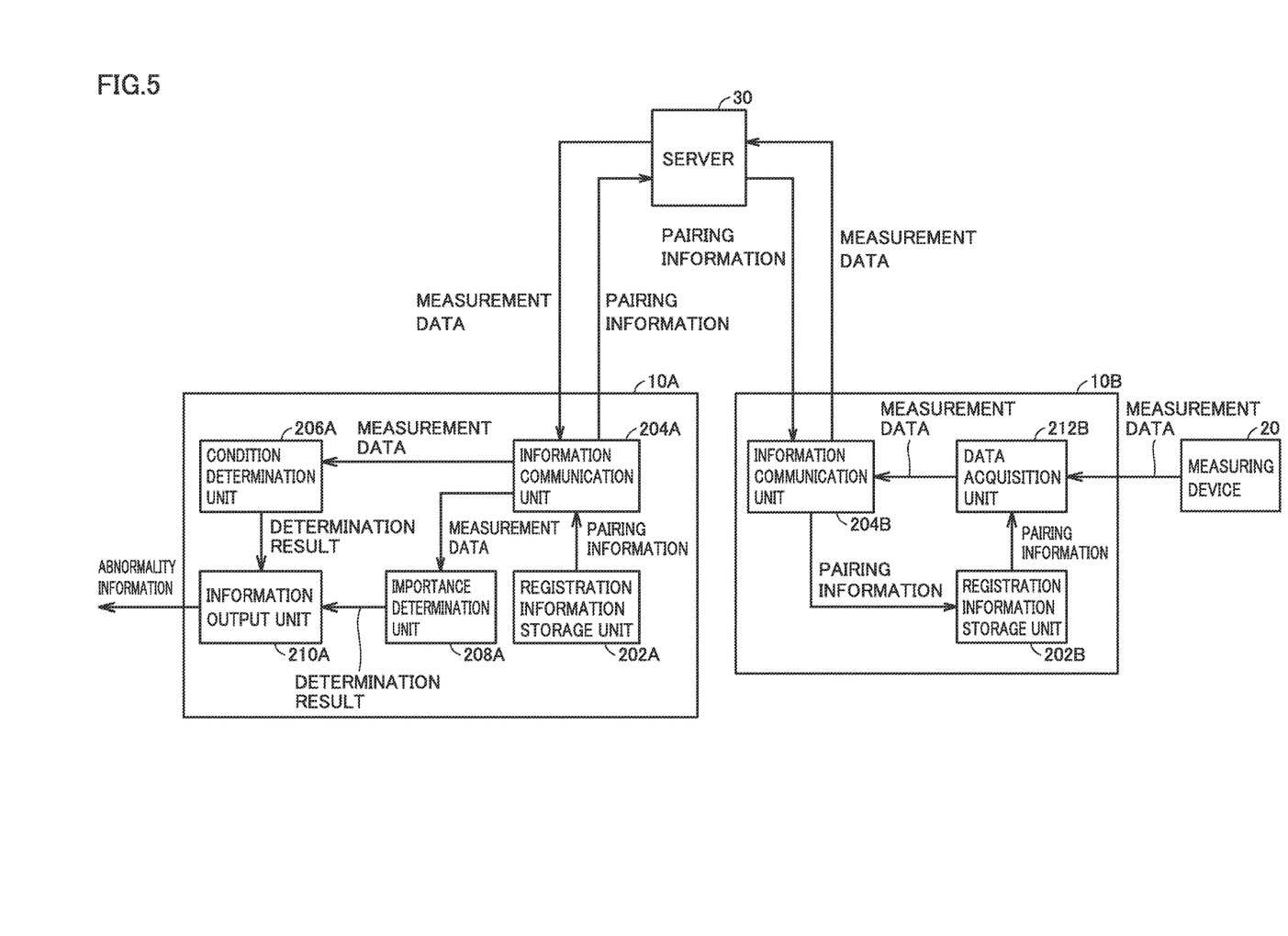
FIG. 5 is a block diagram showing a functional configuration of terminal devices according to the present embodiment.

FIG. 5 is a block diagram showing a functional configuration of terminal devices 10A, 10B according to the present embodiment. Referring to FIG. 5, terminal device 10A includes a registration information storage unit 202A, an information communication unit 204A, a condition determination unit 206A, an importance determination unit 208A, and an information output unit 210A. Terminal device 10B includes a registration information storage unit 202B, an information communication unit 204B, and a data acquisition unit 212B. The functions of terminal devices 10A and 10B are implemented by, for example, processor 152 of each terminal device 10 executing a program stored in memory 154. These functions may be implemented entirely or partially by hardware.

Registration information storage unit 202A of terminal device 10A stores pairing information for establishing wireless communication connection between terminal device 10A and measuring device 20. Information communication unit 204A transmits pairing information and terminal ID a of terminal device 10A to server 30. Here, since terminal ID a is associated with group ID x (terminal device 10A belongs to group X), server 30 stores the received pairing information into database 32 in association with group ID x.

Information communication unit 204B of terminal device 10B acquires pairing information from server 30. Specifically, information communication unit 204B transmits a data acquisition request including terminal ID b of terminal device 10B to server 30. Here, since terminal ID b is associated with group ID x (terminal device 10B belongs to group X), server 30 accepts the data acquisition request and then transmits the information (here, pairing information) associated with group ID x to information communication unit 204B. Information communication unit 204B then receives the pairing information from server 30 and stores the received paring information into registration information storage unit 202B. Information communication unit 204B may accept an instruction of user B to make a data acquisition request to server 30 or may make a data acquisition request periodically.

Data acquisition unit 212B establishes wireless communication connection with measuring device 20 using pairing information and thereafter acquires measurement data of biological information measured by measuring device 20. Specifically, data acquisition unit 212B acquires measurement data of biological information of user B.

Measurement data includes information indicating the type of biological information (for example, blood pressure, body temperature), a measured value of biological information (numerical information), and information indicating the measurement timing (for example, the date and time of measurement). For example, measurement data of sphygmomanometer 21 includes systolic blood pressure/diastolic blood pressure and pulse rate (measured value), and the date and time of measurement. Measurement data of sleep monitor 22 includes sleep duration and the number of times of roll-over (measured value), and the date and time of measurement. Measurement data of pedometer 23 includes step count (measured value) and the date and time of measurement. Measurement data of weight scale and body composition monitor 24 includes weight, body fat rate, and muscle mass amount (measured value), and the date and time of measurement. Measurement data of thermometer 25 includes body temperature (measured value) and the date and time of measurement. Information indicated by the measurement timing may be the date of measurement alone or may be the time of measurement alone.

Information communication unit 204B transmits measurement data of biological information of user B acquired by data acquisition unit 212B (hereinafter simply referred to as "measurement data Db") and terminal ID b to server 30. Server 30 stores measurement data Db into database 32 in association with group ID x.

Information communication unit 204A of terminal device 10A receives measurement data Db from server 30. Specifically, information communication unit 204A transmits a data acquisition request including terminal ID a of terminal device 10A to server 30. Server 30 accepts the data acquisition request and then transmits information associated with group ID x (here, measurement data Db) to information communication unit 204A. Information communication unit 204A thus receives measurement data Db from server 30. Information communication unit 204A may accept an instruction of user A to make a data acquisition request to server 30 or may make a data acquisition request periodically.

Condition determination unit 206A determines whether the health condition of user B is normal or abnormal based on measurement data Db received by information communication unit 204A. Specifically, condition determination unit 206A refers to an information table 600 as shown in FIG. 6 to determine the health condition of user B.

Figure 6:
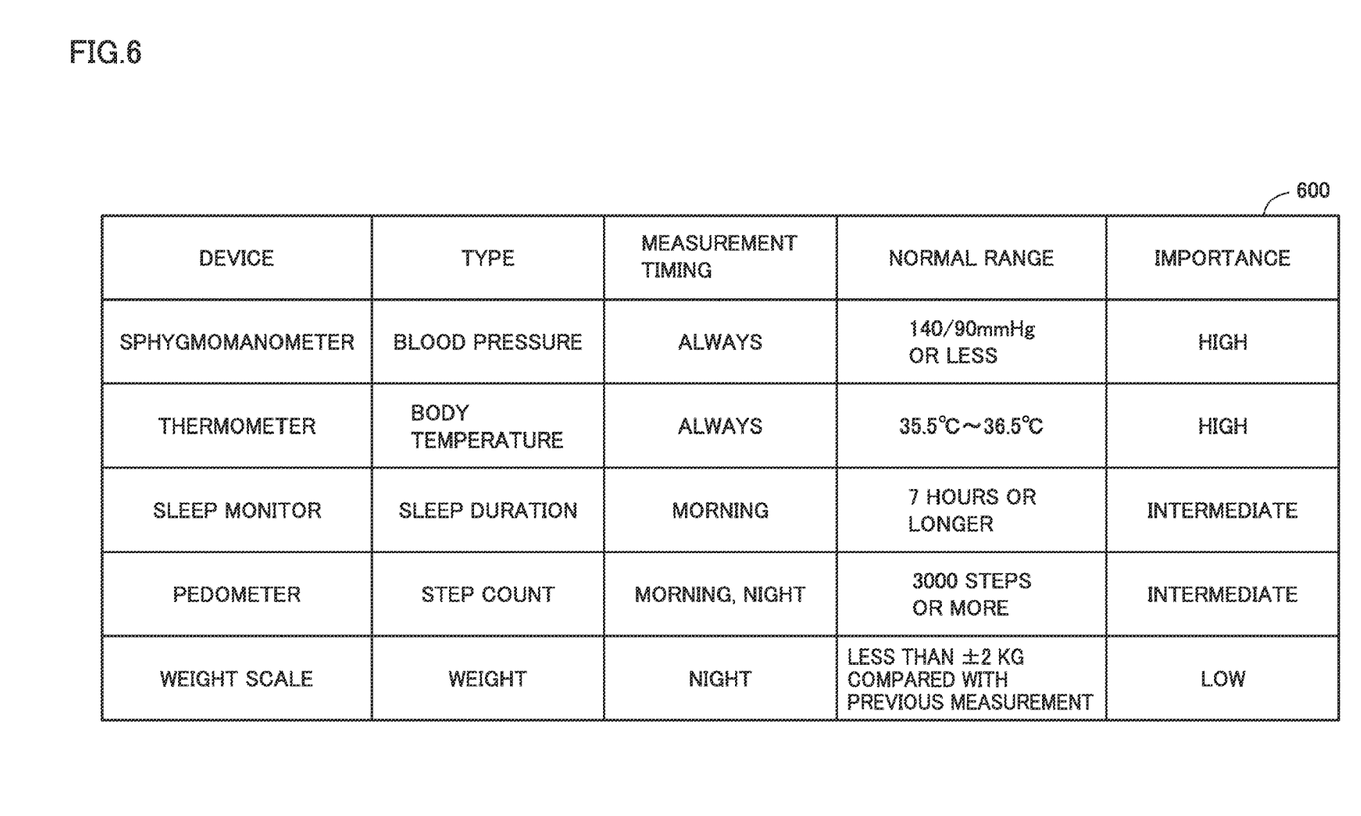
FIG. 6 is a diagram showing an information table according to the present embodiment.

FIG. 6 is a diagram showing information table 600 according to the present embodiment. Referring to FIG. 6, information table 600 is information referred to for determining the health condition of user B. Specifically, information table 600 stores the type of measurement data by each measuring device 20 (the type of the measured biological information), the measurement timing, the normal range of the measured value, and the importance of measurement data in association with each other.

When biological information is blood pressure (measurement data is blood pressure data), the measurement timing is set to "always", and the normal systolic blood pressure and diastolic blood pressure are set to 140 mmHg or less and 90 mmHg or less, respectively. In this case, the blood pressure is measured at regular intervals (for example, every few minutes) and the measured blood pressure is preferably 140 mmHg/90 mmHg or less. When the biological information is a step count, the measurement timing is set to "morning, night" and the normal range is set to 3000 steps or more. In this case, the step count is measured during the day (for example, from 11:00 to 15:00) and during the night (for example, from 19:00 to 23:00) and each measured step count is preferably 3000 steps or more.

For example, three levels of importance "high", "intermediate", and "low" are set, according to the type of measurement data. Typically, the importance of measurement data of biological information that is thought to have a significant impact on life is set to be high. In the present embodiment, the importance of measurement data of blood pressure and body temperature are set to "high", the importance of measurement data of sleep duration and step count are set to "intermediate", and the importance of measurement data of weight is set to "low". In general, biological information having a significant impact on life need to be monitored more frequently. Therefore, the measurement data of biological information (for example, blood pressure, body temperature) for which the interval of measurement timing is set to be shorter than a reference time (for example, one hour) has importance higher than the measurement data of biological information (sleep duration, step count, weight) for which the interval is set to be equal to or longer than a reference value.

The contents of information table 600 (type, measurement timing, normal range, and importance) can be set as desired by user A in accordance with the health condition of user B as a care receiver. The contents of information table 600 may be set by user B himself/herself.

Referring now to FIG. 5 and FIG. 6, in aspect, when the measured value included in measurement data Db falls within a predetermined range (within a normal range in information table 600), condition determination unit 206A determines that the health condition of user B is normal and otherwise determines that the health condition of user B is abnormal.

In another aspect, condition determination unit 206A determines whether biological information of user B is being measured at predetermined timing, based on the date and time of measurement included in measurement data Db. Specifically, condition determination unit 206A checks the date and time of measurement included in measurement data Db and determines whether the biological information is being measured in accordance with the measurement timing shown in information table 600.

For example, when measurement data Db is blood pressure data, condition determination unit 206A determines whether blood pressure is being measured at regular time intervals. When measurement data Db is step count data, condition determination unit 206A determines whether a step count is being measured during the day and during the night. When it is determined that biological information of user B is not being measured at predetermined timing, condition determination unit 206A determines that the health condition of user B is abnormal.

In yet another aspect, condition determination unit 206A may determine that the health condition of user B is normal when the measured value included in measurement data Db falls within a predetermined range and biological information of user B is being measured at predetermined timing.

Importance determination unit 208A refers to information table 600 to determine whether the importance of measurement data Db is set to be equal to or higher than a reference level. For example, it is assumed that the reference level is set to "intermediate". In this case, importance determination unit 208A refers to information table 600 and determines that the importance is equal to or higher than a reference level if measurement data Db is measurement data of any one of blood pressure, body temperature, sleep duration, and step count. On the other hand, importance determination unit 208A determines that the importance is lower than a reference level if measurement data Db is data of weight.

Information output unit 210A outputs information about the health condition of user B, at least based on the determination result of condition determination unit 206A. Specifically, in an aspect, when condition determination unit 206A determines that the health condition of user B is abnormal, information output unit 210A outputs abnormality information indicating that the health condition is abnormal. When condition determination unit 206A determines that the health condition of user B is normal, information output unit 210A may output normality information indicating that the health condition is normal. For example, information output unit 210A displays abnormality information (or normality information) on display 158 or may output abnormality information (or normality information) by sound through speaker 168.

In another aspect, when condition determination unit 206A determines that the health condition of user B is abnormal and importance determination unit 208A determines that the importance of measurement data Db is equal to or higher than a reference level, information output unit 210A may output the abnormality information. Specifically, even when an abnormal value is measured for biological information (for example, weight) of low importance, the level of the abnormality of the health condition of user B is often not such a level that threatens life. Therefore, in such a case, abnormality information is not output. This can alleviate the processing load on terminal device 10A of the caregiver and the burden of monitoring by the caregiver user A.

<Process Procedure>

Figure 7:
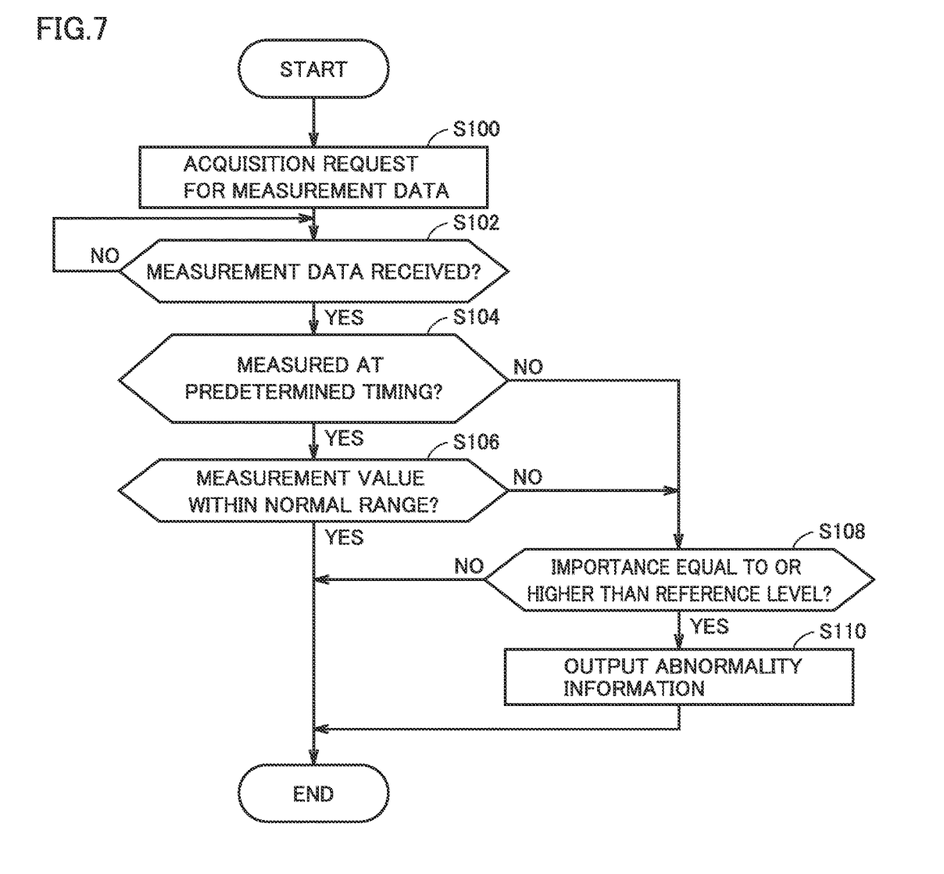
FIG. 7 is a flowchart showing an exemplary process procedure of the terminal device according to the present embodiment.

FIG. 7 is a flowchart showing an exemplary process procedure of terminal device 10A according to the present embodiment. Typically, each step in FIG. 7 is executed by processor 152 of terminal device 10A.

Referring to FIG. 7, terminal device 10A transmits an acquisition request for measurement data Db of biological information of user B to server 30 through communication interface 166 (step S100). Terminal device 10A determines whether measurement data Db has been received from server 30 (step S102). If measurement data Db has not been received (NO in step S102), terminal device 10A repeats the processing in step S102. If measurement data Db has been received (YES in step S102), terminal device 10A determines whether biological information of user B is being measured at predetermined timing, based on measurement data Db and information table 600 (step S104). Specifically, terminal device 10A makes the determination, based on information table 600 and at least one of the time of measurement and the date of measurement included in measurement data Db.

When it is not being measured at predetermined timing (NO in step S104), the processing in step S108 described later is executed. When it is being measured at predetermined timing (YES in step S104), terminal device 10A determines whether the measured value included in measurement data Db falls within a normal range (step S106). When the measured value falls within a normal range (YES in step S106), terminal device 10A terminates the processing. That is, terminal device 10A terminates the processing without outputting information about the health condition of user B.

On the other hand, when the measured value does not fall within a normal range (NO in step S106), terminal device 10A determines whether the importance of measurement data Db is equal to or higher than a reference level (step S108). When the importance is lower than a reference level (NO in step S108), terminal device 10A terminates the processing. On the other hand, when the importance is equal to or higher than a reference level (YES in step S108), terminal device 10A displays abnormality information on display 158 or outputs abnormality information by sound through speaker 168 (step S110). The processing then ends.

According to the description above, when the health condition of user B is normal or when it is determined that the health condition of user B is abnormal but the level of abnormality is low, no information is output. On the other hand, when the level of abnormality of the health condition of user B is high, abnormality information is output. This alleviates the processing load on terminal device 10A and the burden of monitoring by user A while enabling user A to monitor the health condition of user B.

In the description above, when biological information of user B is not being measured at predetermined timing (NO in step S106) or when the measured value is not in a normal range (NO in step S108), abnormality information may be output irrespective of the importance level of measurement data Db. That is, step S108 in FIG. 7 may not be performed. Thus, when an event even slightly different from the normal time occurs, abnormality information is output irrespective of the abnormality level of the health condition of user B, enabling user A to grasp the health condition of user B in detail.

In the description above, when biological information of user B is being measured at predetermined timing (YES in step S106) and the measured value is in a normal range (YES in step S108), information may be output indicating that the health condition of user B is normal. This enables user A to promptly grasp that the health condition of user B is normal and thus gives user A relief.

<Advantages>

According to the present embodiment, user A of terminal device 10A can request measurement data Db of biological information of user B of terminal device 10B from server 30 to check the health condition of user B in real time. When the health condition of user B is abnormal, a notice is given to user A through the display or the like, enabling the user A to promptly grasp the abnormality of user B.

According to the present embodiment, the pairing information acquired by terminal device 10A is stored into server 30, and the pairing information is acquired by terminal device 10B. This eliminates the need for user B to perform the operation for establishing wireless communication connection with measuring device 20.

Other Embodiments (1) In the foregoing embodiment, terminal device 10A displays abnormality information on display 158 or outputs abnormality information by sound through speaker 168, as output examples of abnormality information. However, embodiments are not limited to this configuration. Specifically, terminal device 10A may transmit abnormality information to another terminal device different from terminal device 10B. In this configuration, in case user A does not notice abnormality information on terminal device 10A, the user of the other terminal device can grasp abnormality of the health condition of user B.

(2) In the foregoing embodiment, the function of determining whether the health condition of user B is normal (corresponding to condition determination unit 206A in FIG. 5) is provided in terminal device 10A. However, embodiments are not limited to this configuration. For example, the function may be provided in server 30. Specifically, server 30 determines whether the health condition of user B is normal or abnormal, based on information table 600 stored in the internal memory and measurement data Db received from terminal device 10B and transmits the determination result to terminal device 10A. Server 30 may transmit the determination result to terminal device 10A only when the health condition of user B is abnormal. Terminal device 10A outputs the received determination result (abnormality information).

The configuration of importance determination unit 208A may also be provided in server 30. Specifically, server 30 refers to information table 600 to determine whether the importance of measurement data Db is set to be equal to or higher than a reference level and transmits the determination result to terminal device 10A.

(3) In the foregoing embodiment, a program may be provided that allows a computer to function to execute the control illustrated in the flowchart described above. Such a program may be recorded on a non-transitory computer-readable recording medium accompanying the computer, such as a flexible disk, a CD (Compact Disk Read Only Memory), a secondary storage device, a main storage device, and a memory card and provided as a program product. Alternatively, the program may be recorded on a recording medium contained in the computer, such as a hard disk. Alternatively, the program may be downloaded via a network.

The program may invoke necessary modules, of program modules provided as part of the operating system (OS) of the computer, in a predetermined sequence and at predetermined timing to execute the processing. In this case, the program itself does not include the modules but may cooperate with the OS to execute the processing. The program according to the present embodiment may embrace such a program that does not include modules.

The program according to the present embodiment may be built in another program. Also in this case, the program itself does not include modules included in another program and cooperates with another program to execute the processing. The program according to the present embodiment may embrace such a program built in another program.

(4) The configuration illustrated as the foregoing embodiment is an example of the configuration of the present invention and may be combined with another known techniques or may be modified, for example, partially omitted without departing from the spirit of the present invention. In the foregoing embodiments, the processing or configuration described in other embodiments may be applied as appropriate and carried out.

<Supplementary Notes>

According to an embodiment, a terminal device configured to be able to communicate with a server having a database of biological information measured by a biological information measuring device is provided. The database includes measurement data of biological information of a user of another terminal that is transmitted from the other terminal device to the server. The terminal device includes a reception unit configured to receive the measurement data from the server, a condition determination unit configured to determine whether a health condition of the user is normal or abnormal, based on the measurement data received by the reception unit, and an information output unit configured to output information about a health condition of the user, at least based on a determination result of the condition determination unit.

Preferably, the measurement data includes at least one of a time of measurement and a date of measurement of biological information of the user. When it is determined that biological information of the user is not being measured at predetermined timing, based on at least one of the time of measurement time and the date of measurement, the condition determination unit determines that a health condition of the user is abnormal.

Preferably, the measurement data further includes a measured value of biological information of the user. When it is determined that the measured value falls within a predetermined range and it is determined that biological information of the user is being measured at predetermined timing, the condition determination unit determines that a health condition of the user is normal.

Preferably, the terminal device further includes an importance determination unit configured to determine whether importance of the measurement data is equal to or higher than a reference level. When a health condition of the user is abnormal and the importance is equal to or higher than the reference level, the information output unit outputs abnormality information indicating that a health condition of the user is abnormal.

Preferably, output of the abnormality information includes at least one of display of the abnormality information on a display included in the terminal device and transmission of the abnormality information to another terminal device different from the other terminal device.

Preferably, the terminal device further includes an information storage unit configured to store pairing information for establishing wireless communication connection between the terminal device and the biological information measuring device, and an information transmission unit configured to transmit the pairing information to the server.

An information processing system according to another embodiment includes a server having a database of biological information measured by a biological information measuring device, and a first terminal device and a second terminal device each configured to communicate with the server. The second terminal device includes a data acquisition unit configured to acquire measurement data of biological information of a user of the second terminal device that is measured by the biological information measuring device, from the biological information measuring device, and an information transmission unit configured to transmit the measurement data acquired by the data acquisition unit to the server. The first terminal device includes a reception unit configured to receive the measurement data from the server, a condition determination unit configured to determine whether a health condition of the user is normal, based on the measurement data received by the reception unit, and an information output unit configured to output information about a health condition of the user, at least based on a determination result of the condition determination unit.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A terminal device configured to be able to communicate with a server having a database of biological information measured by a biological information measuring device,
the database including measurement data of biological information of a user of another terminal, the measurement data being transmitted from the other terminal device to the server,
the terminal device comprising:
a reception unit configured to receive the measurement data from the server;
a condition determination unit configured to determine whether a health condition of the user is normal or abnormal, based on the measurement data received by the reception unit;
an information output unit configured to output information about a health condition of the user, at least based on a determination result of the condition determination unit; and
an importance determination unit configured to determine whether importance of the measurement data is equal to or higher than a reference level, wherein
the measurement data includes at least one of a time of measurement and a date of measurement of biological information of the user,
importance of the measurement data is set in accordance with a type of biological information corresponding to the measurement data and an interval of measurement timing of biological information corresponding to the measurement data, and
when a health condition of the user is abnormal and the importance is equal to or higher than the reference level, the information output unit outputs abnormality information indicating that a health condition of the user is abnormal.

2. The terminal device according to claim 1, wherein when it is determined that biological information of the user is not being measured at predetermined timing, based on at least one of the time of measurement time and the date of measurement, the condition determination unit determines that a health condition of the user is abnormal.

3. The terminal device according to claim 2, wherein
the measurement data further includes a measured value of biological information of the user, and
when it is determined that the measured value falls within a predetermined range and it is determined that biological information of the user is being measured at predetermined timing, the condition determination unit determines that a health condition of the user is normal.

4. The terminal device according to claim 1, wherein output of the abnormality information includes at least one of display of the abnormality information on a display included in the terminal device and transmission of the abnormality information to another terminal device different from the other terminal device.

5. The terminal device according to claim 1, further comprising:
an information storage unit configured to store pairing information for establishing wireless communication connection between the terminal device and the biological information measuring device; and
an information transmission unit configured to transmit the pairing information to the server.

6. An information processing system comprising:
a server having a database of biological information measured by a biological information measuring device; and
a first terminal device and a second terminal device each configured to communicate with the server,
the second terminal device including
a data acquisition unit configured to acquire measurement data of biological information of a user of the second terminal device from the biological information measuring device, the biological information being measured by the biological information measuring device, and
an information transmission unit configured to transmit the measurement data acquired by the data acquisition unit to the server,
the first terminal device including
a reception unit configured to receive the measurement data from the server,
a condition determination unit configured to determine whether a health condition of the user is normal, based on the measurement data received by the reception unit,
an information output unit configured to output information about a health condition of the user, at least based on a determination result of the condition determination unit, and
an importance determination unit configured to determine whether importance of the measurement data is equal to or higher than a reference level, wherein
the measurement data includes at least one of a time of measurement and a date of measurement of biological information of the user,
the importance of the measurement data is set in accordance with a type of biological information corresponding to the measurement data and an interval of measurement timing of biological information corresponding to the measurement data, and
when a health condition of the user is abnormal and the importance is equal to or higher than the reference level, the information output unit outputs abnormality information indicating that a health condition of the user is abnormal.

* * * * *